United States Patent
Katafuchi et al.

[11] Patent Number: 5,948,225
[45] Date of Patent: Sep. 7, 1999

[54] OXYGEN SENSOR ELEMENT

[75] Inventors: Toru Katafuchi, Kariya; Kiyomi Kobayashi, Kuwana; Naoto Miwa, Tsushima; Hiromi Sano, Nagoya; Toshitaka Saito, Toyohashi, all of Japan

[73] Assignee: Denso Corporation, Japan

[21] Appl. No.: 08/861,226

[22] Filed: May 21, 1997

[30] Foreign Application Priority Data

May 21, 1996 [JP] Japan ............................ 8-150255

[51] Int. Cl.$^6$ .................................................. G01N 27/407
[52] U.S. Cl. ........................ 204/421; 204/424; 204/426; 204/428; 204/429; 427/58; 427/125; 427/229; 427/443.1
[58] Field of Search ...................... 204/421–429

[56] References Cited

U.S. PATENT DOCUMENTS

| | | | |
|---|---|---|---|
| 3,978,006 | 8/1976 | Topp et al. ............................ | 204/429 |
| 4,199,425 | 4/1980 | Sinkevitch ............................ | 204/429 |
| 4,225,634 | 9/1980 | Tanaka et al. ........................ | 204/429 |
| 4,265,724 | 5/1981 | Haecker et al. ...................... | 204/429 |
| 5,472,591 | 12/1995 | Saito et al. .......................... | 204/429 |
| 5,716,507 | 2/1998 | Tanaka et al. ........................ | 204/429 |

FOREIGN PATENT DOCUMENTS 4-95766   3/1992   Japan .

Primary Examiner—T. Tung
Attorney, Agent, or Firm—Pillsbury Madison & Sutro LLP

[57] ABSTRACT

An oxygen sensor element includes a solid electrolyte having cavities on a surface thereof and an electrode formed on the surface of the solid electrolyte. In a method of producing the oxygen sensor element, a solution containing a noble metal compound for nucleus formation is first applied to an electrode forming portion of the solid electrolyte to form a coating film. Then, the coating film is heat-treated to form a nucleus forming portion where noble metal nuclei are deposited. Subsequently, metal plating is applied to the nucleus forming portion to form a plating film deeply entering the cavities. Thereafter, the plating film is burned to form the electrode deeply entering the cavities.

1 Claim, 13 Drawing Sheets

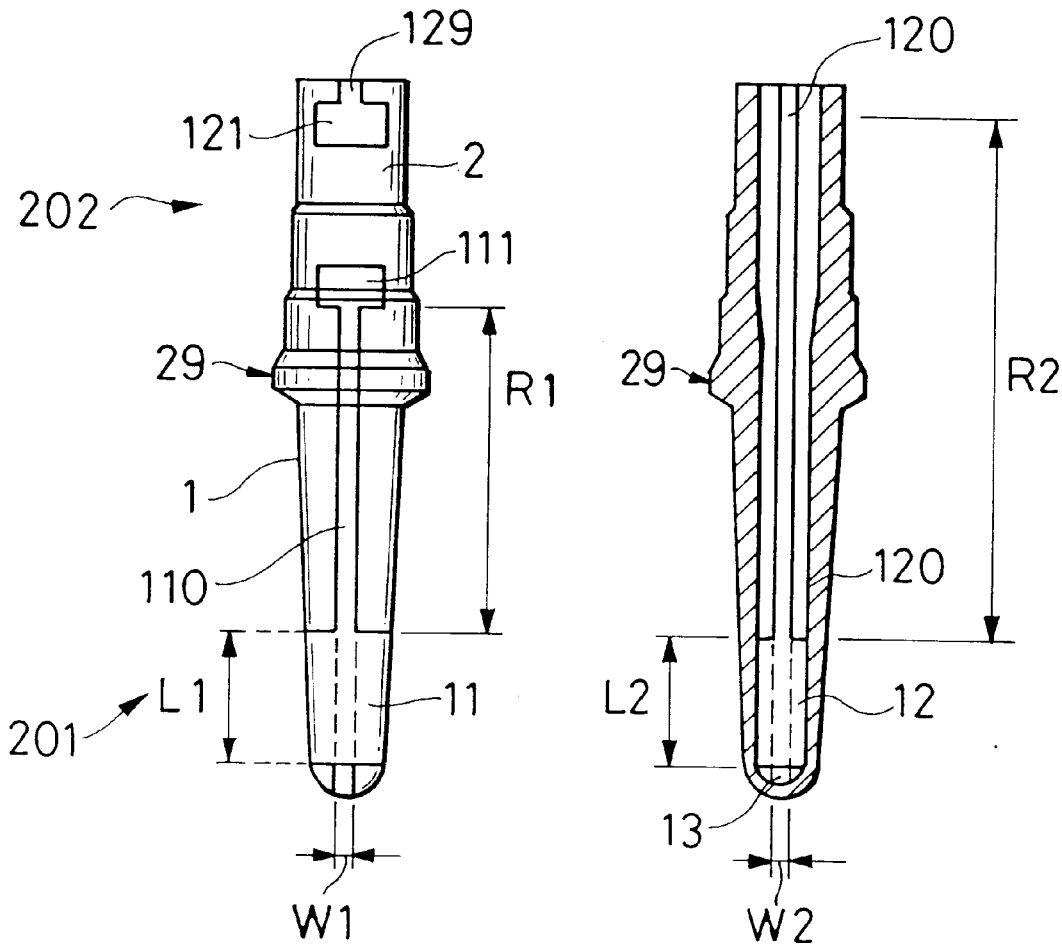
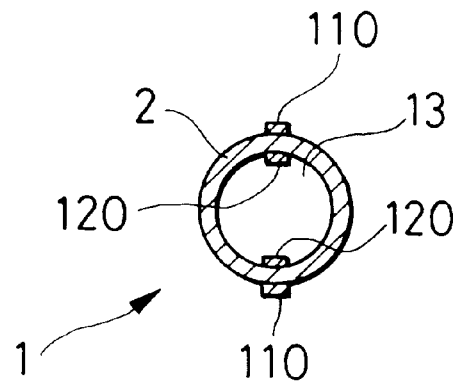

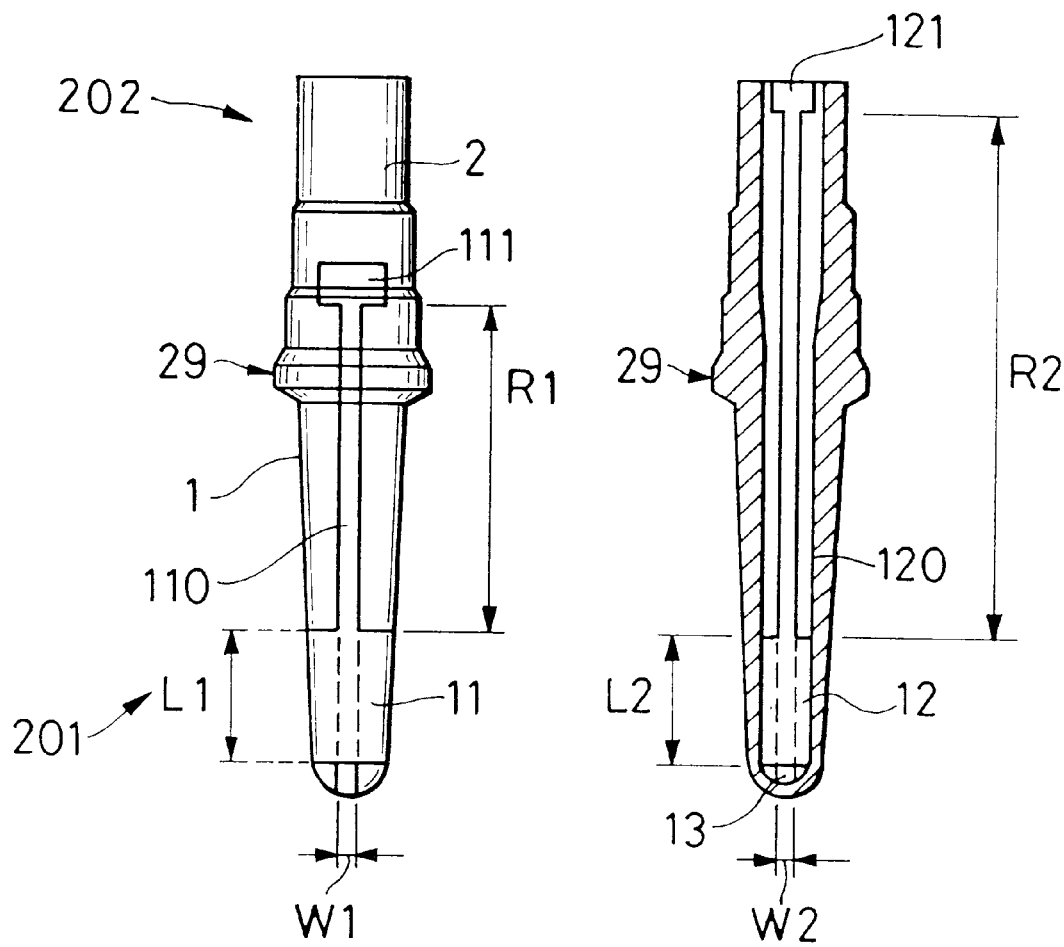
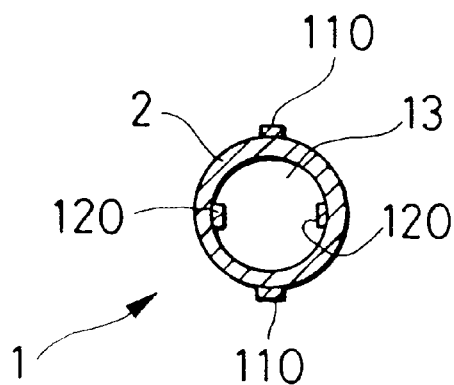

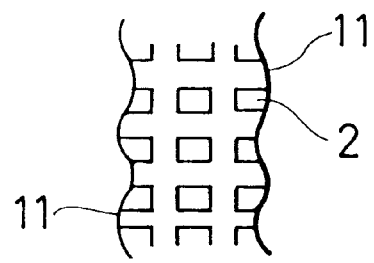
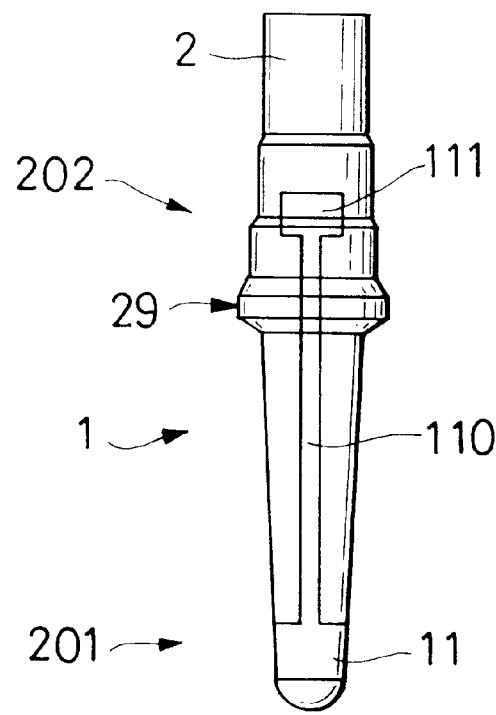
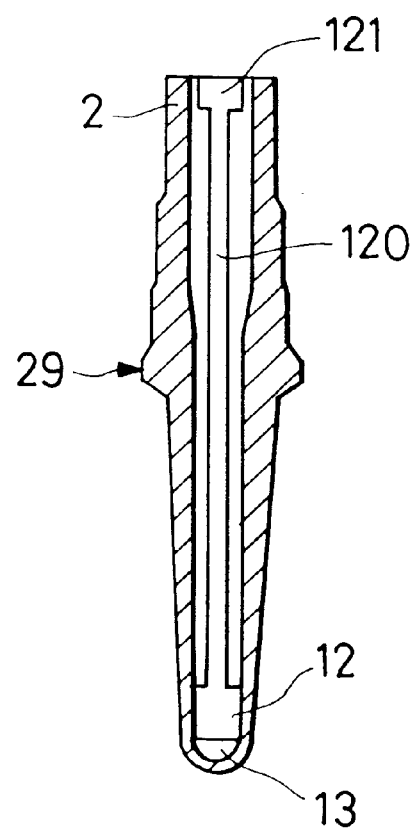

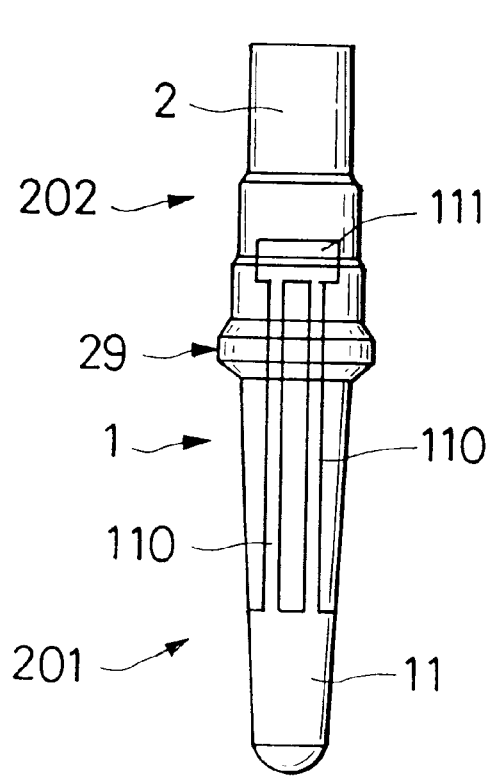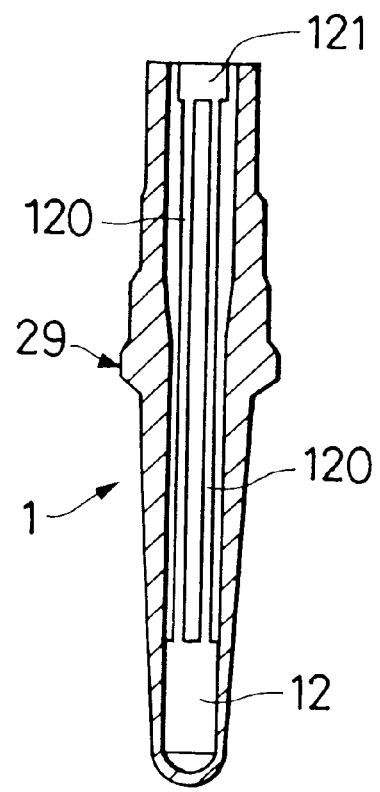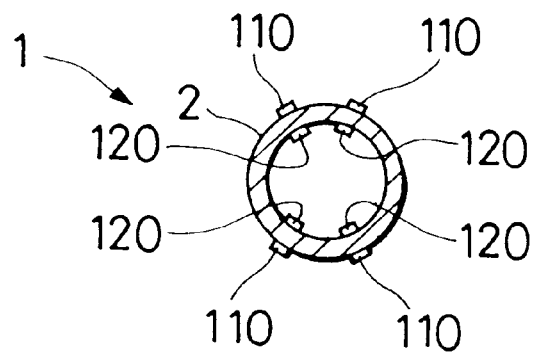

OXYGEN SENSOR ELEMENT

BACKGROUND OF THE INVENTION

1. Field of the Invention

The present invention relates to an oxygen sensor element which can be used in an air-fuel ratio control for an automobile engine, and further relates to a method of producing such an oxygen sensor element.

2. Description of the Prior Art

In the exhaust system of an automobile engine, an oxygen sensor is provided for measuring the oxygen concentration in the exhaust gas so as to perform an air-fuel ratio control based on measured values of the oxygen concentration.

The oxygen sensor includes an oxygen sensor element for detecting the oxygen concentration. The oxygen sensor element includes a solid electrolyte and electrodes provided on the solid electrolyte. The electrodes include an internal electrode exposed to a reference gas and an external electrode exposed to a gas to be measured.

For providing the foregoing electrodes at electrode forming portions of the solid electrolyte, the following method has been used:

First, noble metal nuclei are adhered to the electrode forming portions of the solid electrolyte to form nucleus forming portions. Then, metal plating is applied to the nucleus forming portions to form plating films. Thereafter, the plating films are burned to form the foregoing electrodes on the solid electrolyte.

The foregoing nucleus forming portions are achieved by spraying particles of noble metal, such as platinum (Pt), onto the electrode forming portions of the solid electrolyte.

As shown in FIGS. 24A and 24B, a large number of fine holes or cavities are formed on the surface of the solid electrolyte. Accordingly, when the noble metal particles are applied onto the surface of the solid electrolyte at the electrode forming portions thereof, the noble metal particles enter the cavities of the solid electrolyte to form the nucleus forming portions. Thus, upon plating the nucleus forming portions, a plating liquid reacts with the noble metal particles within the cavities so that the plating films are organically tangled with particles of the solid electrolyte to achieve a strong adhesion force therebetween based on an anchor effect. Then, by burning the plating films, the electrodes are achieved which are hard to peel off from the surface of the solid electrolyte.

However, there is the following problem in the foregoing method of forming the nucleus forming portions:

Specifically, there may be formed a complicated pattern, as the foregoing electrode, on the surface of the solid electrolyte as shown, for example, in FIG. 2A and FIG. 9. Accordingly, in the foregoing forming method employing spraying of the noble metal particles, it is necessary to partially mask the surface of the solid electrolyte and thus it is difficult to produce the electrode of a complicated shape.

Japanese First (unexamined) Patent Publication No. 4-95766 discloses another forming method, wherein a solution containing a noble metal compound is applied to the electrode forming portions of the solid electrolyte to form coating films and then, by heating the coating films at a high temperature, those components (for example, a binder) other than the noble metal in the solution are volatilized or decomposed so that only the noble metal nuclei are deposited to form nucleus forming portions.

In the latter forming method, the nucleus forming portion can be easily provided at the electrode forming portion of a desired shape using, for example, screen printing, stamp printing, pad printing, roll transfer, dip method, spray method or dispenser method.

However, the latter forming method has the following problem:

Specifically, since the heating of the coating films is carried out at a high temperature, i.e. about 700° C. or higher, flocculation of the noble metal advances so that the mean particle diameter of the noble metal nuclei becomes 0.1 $\mu$m to 0.8 $\mu$m. Hence, as shown in FIG. 24A, the noble metal nuclei 92 can not enter the fine cavities 21 formed on the surface of the solid electrolyte 2, but stay at entrances of the fine cavities 21.

In this case, as shown in FIG. 24B, the plating film 119 can not advance into the fine cavities 21 so that the adhesion force based on the anchor effect can not be achieved between the plating film 119 and the solid electrolyte 2.

Further, as shown in FIG. 24A, in the latter forming method, the noble metal nuclei 92 are localized on the surface of the solid electrolyte 2. This means that distances between the adjacent noble metal nuclei 92 become large. As appreciated, the adhesion force between the plating film 119 and the solid electrolyte 2 can not be achieved at portions where no noble metal nuclei 92 exist, and thus, in the latter forming method, those portions where the adhesion force can not be achieved exist largely on the surface of the solid electrolyte 2.

Consequently, in the latter forming method, such an oxygen sensor element tends to be produced, wherein the peeling-off of the electrode is liable to occur and the surface resistance at an interface between the electrode and the solid electrolyte 2 is excessively large to disable outputs required for detection of the oxygen concentration.

SUMMARY OF THE INVENTION

Therefore, it is an object of the present invention to provide an oxygen sensor element, wherein an electrode is hard to peel off from a solid electrolyte and the surface resistance at an interface between the electrode and the solid electrolyte is small.

It is another object of the present invention to provide a method of producing such an oxygen sensor element.

According to one aspect of the present invention, an oxygen sensor element comprises a solid electrolyte having cavities on a surface thereof; and an electrode formed on the surface of the solid electrolyte, the electrode deeply entering the cavities for ensuring adhesion of the electrode relative to the surface of the solid electrolyte.

It may be arranged that the electrode is in the form of a plating film produced via noble metal nuclei provided on the surface of the solid electrolyte, the noble metal nuclei having a mean particle diameter which is small enough for the noble metal nuclei to deeply enter the cavities.

It may be arranged that the mean particle diameter of the noble metal nuclei is 0.05 $\mu$m or smaller.

It may be arranged that each of the cavities has finer cavities therein, and that the electrode further enters the finer cavities.

According to another aspect of the present invention, a method of producing an oxygen sensor element which includes a solid electrolyte having cavities on a surface thereof and an electrode formed on the surface of the solid electrolyte, comprises the steps of: applying a solution containing a noble metal compound for nucleus formation to the surface at an electrode forming portion of the solid electrolyte to form a coating film; heat-treating the coating film by heating to form a nucleus forming portion where noble metal nuclei are deposited; plating the nucleus forming portion to form a plating film, the plating film deeply entering the cavities; and burning the plating film to form the electrode so that the electrode deeply enters the cavities.

It may be arranged that the noble metal nuclei have a mean particle diameter which is small enough for the noble metal nuclei to deeply enter the cavities.

It may be arranged that the mean particle diameter of the noble metal nuclei is 0.05 µm or smaller.

It may be arranged that the coating film is heat-treated at a temperature in the range of 200° C. to 600° C.

It may be arranged that the noble metal compound is an organic noble metal compound.

It may be arranged that a concavo-convex treatment is applied to the surface of the solid electrolyte for promoting irregularities to be formed on the surface.

It may be arranged that a concentration of the noble metal compound relative to the solution is 0.05% by weight to 0.4% by weight.

It may be arranged that noble metal in the noble metal compound is at least one selected from the group consisting of Pt, Pd, Au and Rh.

BRIEF DESCRIPTION OF THE DRAWINGS

The present Invention will be understood more fully from the detailed description given hereinbelow, taken in conjunction with the accompanying drawings.

In the drawings:

FIG. 2A is a front view of the oxygen sensor element according to the first embodiment of the present invention;

FIG. 2B is a longitudinal-sectional view of the oxygen sensor element shown in FIG. 2A;

FIG. 3 is a cross-sectional view of the oxygen sensor element at its tip portion shown in FIGS. 2A and 2B;

FIG. 7A is a front view showing a modification of the oxygen sensor element according to the first embodiment of the present invention;

FIG. 7B is a longitudinal-sectional view of the oxygen sensor element shown in FIG. 7A;

FIG. 8 is a cross-sectional view of the oxygen sensor element at its tip portion shown in FIGS. 7A and 7B;

FIG. 13 is an enlarged view of an external electrode of the oxygen sensor element shown in FIGS. 12A and 12B;

FIG. 14A is a front view showing a modification of the oxygen sensor element according to the first embodiment of the present invention;

FIG. 14B is a longitudinal-sectional view of the oxygen sensor element shown in FIG. 14A;

FIG. 15A is a front view showing a modification of the oxygen sensor element according to the first embodiment of the present invention;

FIG. 15B is a longitudinal-sectional view of the oxygen sensor element shown in FIG. 15A;

FIG. 16 is a cross-sectional view of the oxygen sensor element at its tip portion shown in FIGS. 15A and 15B;

DESCRIPTION OF THE PREFERRED EMBODIMENT

Now, preferred embodiments of the present invention will be described hereinbelow with reference to the accompanying drawings. Throughout the figures, the same reference signs represent the same or corresponding elements.

First Embodiment

The first embodiment of the present invention will be described hereinbelow with reference to FIGS. 1A to 6.

As shown in FIGS. 2A and 2B, an oxygen sensor element 1 includes a cylindrical solid electrolyte 2 and electrodes formed on the surface of the solid electrolyte 2. The electrodes include an external electrode 11 formed on an outer periphery of the solid electrolyte 2 and an internal electrode 12 formed on an inner periphery of the solid electrolyte 2.

For producing the oxygen sensor element 1, a solution containing a noble metal compound for nucleus formation is applied to electrode forming portions of the solid electrolyte 2 to form coating films.

Figure 1A:
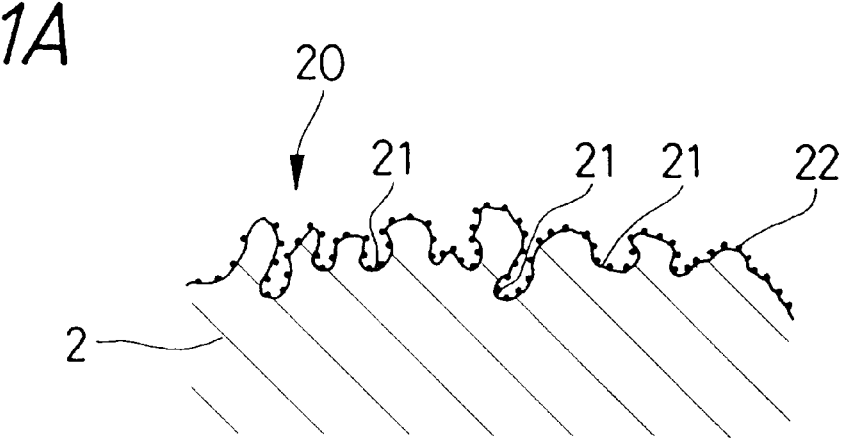
FIG. 1A is an enlarged view of the surface of a solid electrolyte of an oxygen sensor element according to a first embodiment of the present invention.

Then, the coating films are subjected to heat treatment by heating so as to form nucleus forming portions 20 wherein noble metal nuclei 22 are deposited as shown in FIG. 1A (showing only one of the nucleus forming portions 20). The noble metal nuclei 22 are in the form of noble metal spheres or hemispheres obtained by decomposing the noble metal compound contained in the solution through the heat treatment of the coating films so as to deposit on the surface of the solid electrolyte 2.

Then, metal plating is applied to the nucleus forming portions 20 to form plating films 119 thereon. Thereafter, the plating films 119 are burned to achieve the foregoing electrodes 11 and 12.

The mean particle diameter of the noble metal nuclei 22 at the nucleus forming portions 20 is 0.05 $\mu$m or smaller.

Now, the oxygen sensor element 1 will be described in detail.

As shown in FIGS. 2A to 3, the solid electrolyte 2 is closed at its tip to provide a reference gas chamber 13. The solid electrolyte 2 is made of zirconia. As described above, the external electrode 11 is disposed on the outer periphery of the solid electrolyte 2 while the internal electrode 12 is disposed on the inner periphery thereof defining the reference gas chamber 13.

On the outer periphery of the solid electrolyte 2 is provided a collar portion 29 protruding radially outward. At the upper side of the collar portion 29, two steps are formed to provide three diameter-different portions.

As shown in FIG. 2A, the external electrode 11 is formed in a strip shape at a tip portion 201 of the solid electrolyte 2. As shown in FIG. 2B, the internal electrode 12 is formed on the inner periphery at a portion defining the reference gas chamber 13 and corresponding to the external electrode 11. The external electrode 11 is electrically connected to electrode terminals 111 via electrode leads 110 each extending upward from the external electrode 11. Similarly, the internal electrode 12 is electrically connected to electrode terminals 121 via electrode leads 120 each extending upward from the internal electrode 12. The electrode terminals 111 and 121 are formed on the outer periphery of the solid electrolyte 2 at a trunk portion 202 thereof.

As shown in FIG. 7B, the electrode terminals 121 may be formed on the inner periphery of the solid electrolyte 2.

The external electrode 11, the electrode leads 110 and the electrode terminals 111 are formed integral with each other. Similarly, the internal electrode 12, the electrode leads 120 and the electrode terminals 121 are formed integral with each other.

As shown in FIG. 3, the electrode leads 110 are provided in pair and the electrode leads 120 are also provided in pair. The electrode leads 110 and 120 are arranged in pairs in the same radial directions of the solid electrolyte 2 with a phase difference of 180°.

On the other hand, as shown in FIG. 8, the electrode leads 110 and 120 may be arranged in four different radial directions with phase differences of 90°. Further, the number of the electrode leads 110 or 120 may take a value other than two as long as the sensor output can be taken out.

A length L1 of the external electrode 11 and a length L2 of the internal electrode 12 are set equal to each other, each being set to 10 mm. A thickness of each of the electrodes 11 and 12 is set to 1 $\mu$m. Lead widths W1 and W2 of the electrode leads 110 and 120 are set to 1.5 mm, respectively, a length R1 of the electrode lead 110 is set to 23 mm, and a length R2 of the electrode lead 120 is set to 34 mm. Further, each of the electrode terminals 111 and 121 has a rectangular shape with 5 mm by 4 mm. On the other hand, the electrode terminal 111, 121 may take any shape as long as the sensor output can be taken out.

It is preferable that the length L1, L2 is set to 2 mm to 20 mm. If the length L1, L2 is smaller than 2 mm, it is possible that the required sensor output can not be achieved. On the other hand, if the length L1, L2 is greater than 20 mm, it is possible that the sensor output includes an output from a portion (low temperature portion) whose response characteristic is poor so that the whole response characteristic is deteriorated. Further, the cost performance may be possibly lowered.

Now, an oxygen sensor 3 incorporating the foregoing oxygen sensor element 1 will be described.

Figure 6:
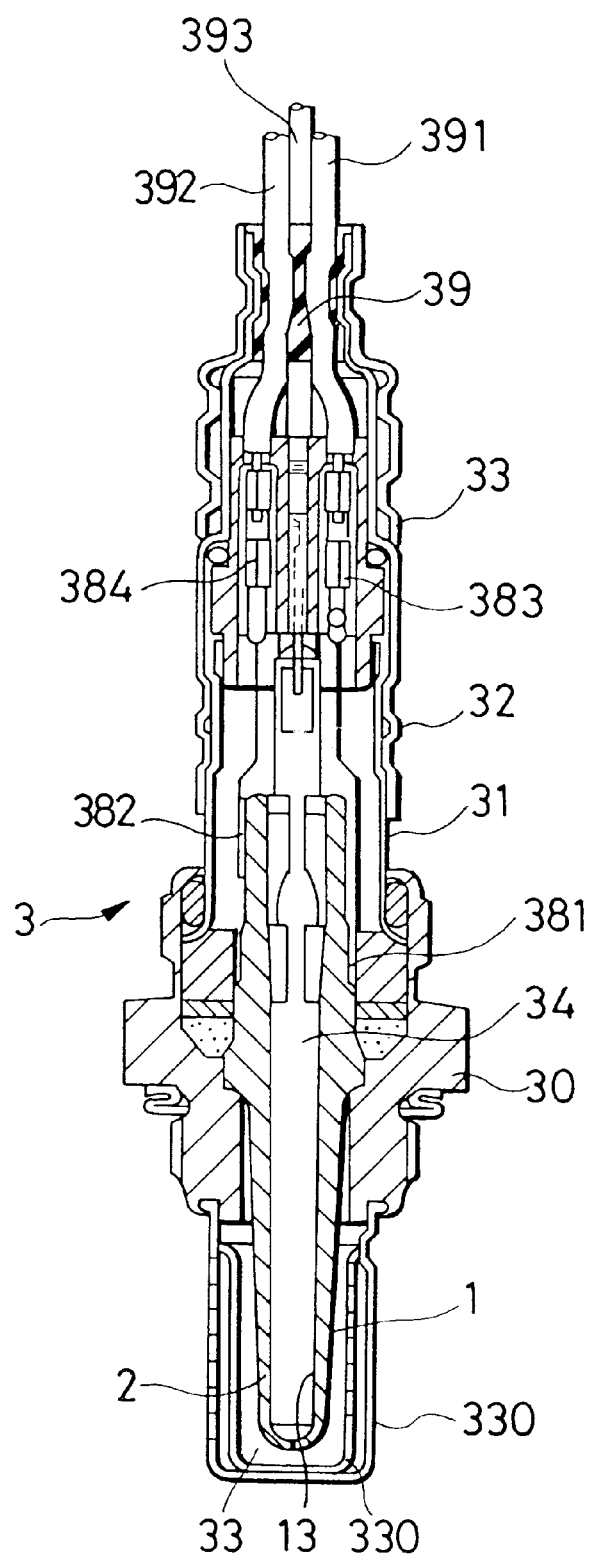
FIG. 6 is a longitudinal-sectional view of an oxygen sensor according to the first embodiment of the present invention.

As shown in FIG. 6, the oxygen sensor 3 includes a housing 30 and the oxygen sensor element 1 received through the housing 30. At the lower side of the housing 30 is formed a to-be-measured gas chamber 33 defined by a to-be-measured gas side cover 330 which is double-structured for protecting the tip portion 201 of the oxygen sensor element 1. At the upper side of the housing 30 are provided three-stage atmosphere side covers 31, 32 and 33.

A rod-shaped heater 34 is received in the reference gas chamber 13 of the oxygen sensor element 1 with given clearances relative to the inner periphery of the solid electrolyte 2 defining the reference gas chamber 13.

An elastic insulating member 39 with leads 391–393 passing therethrough is fitted into the atmosphere side cover 32 at its upper end. The leads 391 and 392 are for taking out a current generated through the solid electrolyte 2 as a signal and sending it out to the exterior. On the other hand, the lead 393 is for energizing the heater 34 to generate heat.

At the lower ends of the leads 391 and 392 are provided connecting terminals 383 and 384 which are electrically connected to terminals 381 and 382 fixed to the oxygen sensor element 1. The terminals 381 and 382 are in abutment with the foregoing electrode terminals 111 and 121 of the oxygen sensor element 1.

Now, a method of producing the foregoing oxygen sensor element 1 will be described in detail.

As described before, the external electrode 11, the electrode leads 110 and the electrode terminals 111 are formed integral with each other, and the internal electrode 12, the electrode leads 120 and the electrode terminals 121 are formed integral with each other. Accordingly, each of the electrode forming portions of the solid electrolyte 2 includes not only a portion where the electrode 11, 12 is formed, but also those portions where the electrode leads 110, 120 and the electrode terminals 111, 121 are formed.

First, zirconia is formed into a shape as shown in FIGS. 2A and 2B and then provisionally burned to obtain the solid electrolyte 2 in the form of a zirconia sintered body ($ZrO_2$—$Y_2O_3$). The solid electrolyte 2 may be made of other materials as long as ionic conductivity is achieved. Subsequently, a solution containing a noble metal compound is applied to the electrode forming portions on the inner and outer peripheries of the solid electrolyte 2 to form coating films (see FIGS. 2A and 2B).

As the noble metal compound, an organic platinum compound, such as dibenzylidene platinum ($C_{16}H_{16}Pt$), is used. In the foregoing solution, the organic platinum compound is contained at 0.4% by weight. Other than the organic platinum compound, the solution contains an acrylic binder and terpineol.

The dispenser method is used for applying the foregoing solution to the electrode forming portion on the inner periphery. On the other hand, the pad printing is carried out several times for applying the foregoing solution to the electrode forming portion on the outer periphery.

Figures 4A, 4B:
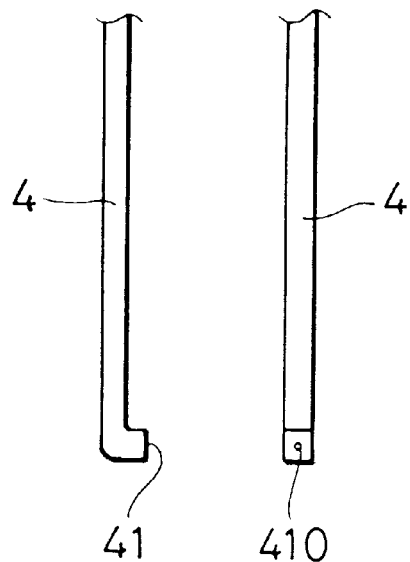
FIG. 4A is a front view of a nozzle to be used upon forming an electrode according to the first embodiment of the present invention.
FIG. 4B is a side view of the nozzle shown in FIG. 4A.

In the dispenser method, a nozzle 4 having an inside passage and as shown in FIGS. 4A and 4B is used. A tip portion 41 of the nozzle 4 is bent by an angle of about 90° and formed at its center with an injection hole 410 for injecting the solution.

First, the nozzle 4 is inserted into the solid electrolyte 2 near the bottom of the reference gas chamber 13. Upon insertion of the nozzle 4, the solution is applied to the electrode forming portion for one of the electrode leads 120. Then, at that position, the solution is further applied while moving the tip portion 41 of the nozzle 4 vertically and circumferentially relative to the inner periphery of the solid electrolyte, so as to complete application of the solution for the internal electrode 12.

Then, while injecting the solution from the tip portion 41, the nozzle 4 is moved upward of the reference gas chamber 13. At this time, the tip portion 41 of the nozzle 4 is not moved circumferentially relative to the inner periphery of the solid electrolyte 2.

Through the foregoing operation, the application of the solution to the electrode forming portion for the internal electrode 12 and the pair of electrode leads 120 (see FIG. 3) is completed.

Thereafter, the solution is applied to the electrode forming portion for lead portions 129 (see FIG. 2A) drawing out the corresponding electrode leads 120 to the outer periphery of the solid electrolyte 2 and for the electrode terminals 121 on the outer periphery of the solid electrolyte 2 near its upper end, and then the application of the solution is completed.

Figures 5A, 5B:
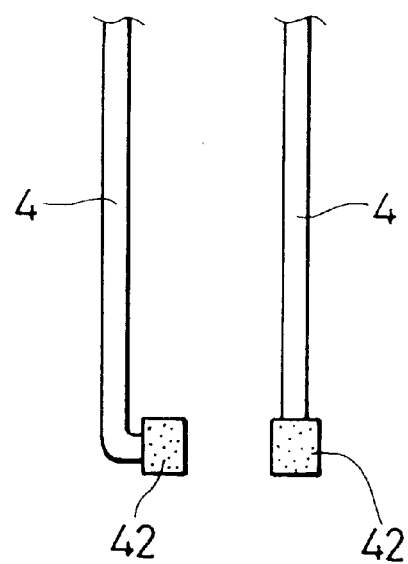
FIG. 5A is a front view showing a modification of the nozzle shown in FIGS. 4A and 4B.
FIG. 5B is a side view of the nozzle shown in FIG. 5A.

Instead of the nozzle 4 shown in FIGS. 4A and 4B, a nozzle 4 shown in FIGS. 5A and 5B may be used. A tip portion of the nozzle 4 in FIGS. 5A and 5B includes a porous member 42. Through pores of the porous member 42, the solution is injected and applied to the electrode forming portion.

Subsequently, the coating films at the electrode forming portions are dried.

Then, the coating films are subjected to heat treatment at 400° C. for decomposing the organic platinum compound contained in the coating films so as to deposit the noble metal nuclei, i.e. the platinum nuclei at the foregoing electrode forming portions, while removing the other components, such as the binder, through volatilization or decomposition.

Figure 1B:
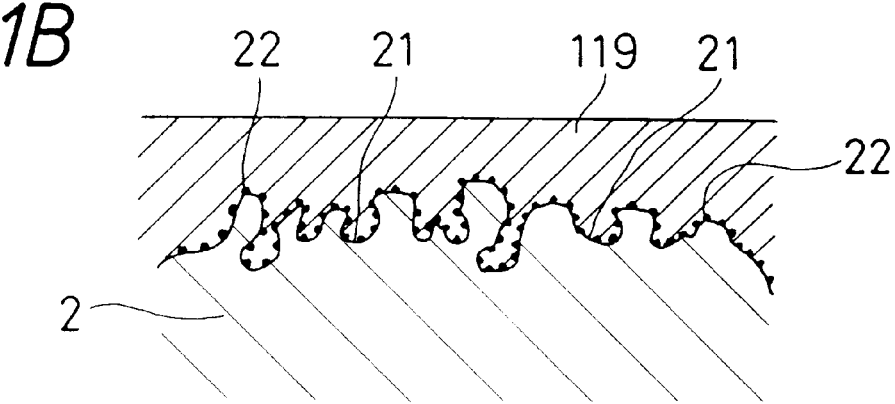
FIG. 1B is an enlarged view of a plating film formed on the surface of the solid electrolyte shown in FIG. 1A.
Figure 1C:
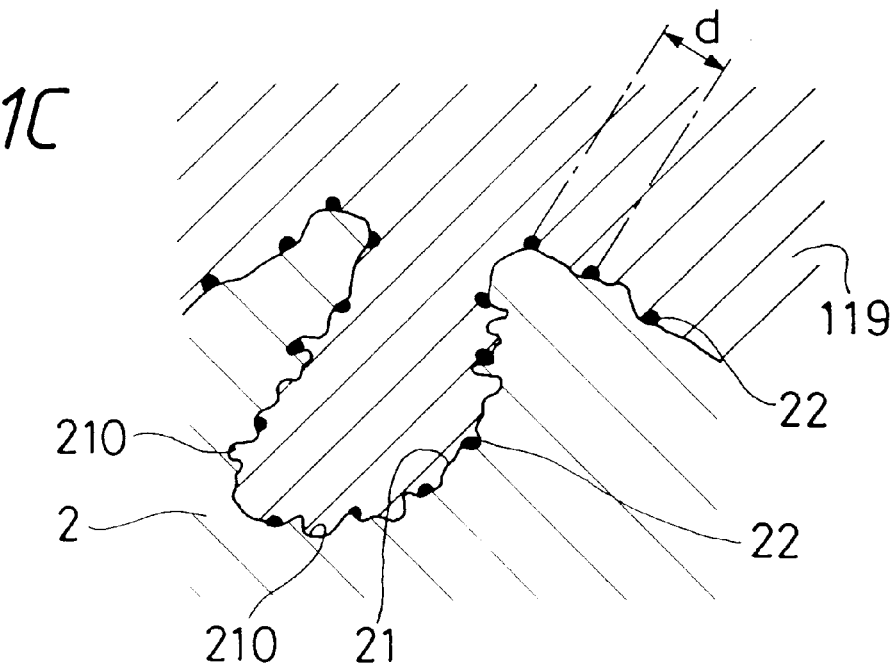
FIG. 1C is an enlarged view of a fine hole or cavity formed on the surface of the solid electrolyte shown in FIG. 1B.

Through the foregoing operation, as shown in FIGS. 1A to 1C, the nucleus forming portions 20 are formed wherein the noble metal nuclei 22 are uniformly dispersed and further deeply enter fine holes or cavities 21 which are formed in large number on the surface of the solid electrolyte 2.

Then, as shown in FIG. 1B, electroless plating of platinum is applied to the nucleus forming portions 20 to form the plating films 119. The plating film 119 may be made of noble metal, other than platinum, such as palladium (Pd), gold (Au) and rhodium (Rh). It is not necessary that the plating film is made of the same material as the noble metal nucleus. Upon plating, the noble metal nuclei 22 react with the noble metal contained in a plating liquid so as to facilitate formation of the plating films 119. Since the noble metal nuclei 22 deeply enter the fine cavities 21, the plating liquid and thus the plating films 119 also deeply enter the fine cavities 21. Thereafter, the plating films 119 together with the solid electrolyte 2 are burned at 1,000° C. to achieve the external and internal electrodes 11 and 12, the electrode leads 110 and 120 and the electrode terminals 111 and 121 which also deeply enter the fine cavities 21.

Through the foregoing operation, the oxygen sensor element 1 according to the first embodiment is obtained.

The oxygen sensor element 1 has the following advantages:

As described above, a large number of the fine cavities 21 are formed on the surface of the solid electrolyte 2 as shown in FIG. 1A. On the other hand, as described before, the mean particle diameter of the noble metal nuclei 22 produced through the foregoing operation is no greater than 0.05 $\mu$m which is much smaller as compared with the fine cavities 21. Accordingly, the noble metal nuclei 22 can deeply enter the fine cavities 21. Further, as best shown in FIG. 1C, the noble metal nuclei 22 can even enter finer holes or cavities 210 formed within the fine cavities 21.

Further, a distance d between the adjacent noble metal nuclei 22 is very small. This means that the noble metal nuclei 22 are not localized but dispersed uniformly over the electrode forming portions to form the nucleus forming portions 20.

For this reason, each of the plating films 119 formed on the nucleus forming portions 20 can be securely adhered to the solid electrolyte 2 based on a strong anchor effect achieved at an interface between the plating film 119 and the solid electrolyte 2. Accordingly, a strong adhesion force can be achieved between the solid electrolyte 2 and each of the external and internal electrodes 11 and 12 which are obtained by burning the plating films 119. Hence, the external and internal electrodes 11 and 12 are hard to peel off from the surface of the solid electrolyte 2.

Further, since the noble metal nuclei 22 are dispersed uniformly all over the nucleus forming portions 20, the foregoing strong adhesion force is exerted all over the interface between the solid electrolyte 2 and each of the external and internal electrodes 11 and 12. Thus, the surface resistance at the interface therebetween is made small. This is also applied to the electrode leads 110 and 120 and the electrode terminals 111 and 121.

In the foregoing first embodiment, the dispenser method and the pad printing are used for applying the solution to the electrode forming portions. On the other hand, it may be arranged to use at least one of the screen printing, the stamp printing, the roll transfer, the dip method and the spray method for applying the solution to the electrode forming portions.

It is preferable to use the pad printing or the roll transfer since a coating film of a desired shape can be easily formed on a curved surface, such as the inner/outer periphery of the cylindrical solid electrolyte, and further a coating film can be formed with accuracy.

In the foregoing first embodiment, the heat treatment to the coating films is performed at 400° C. It is preferable that the heat treatment to the coating films is performed at a temperature in the range of 200° C. to 600° C.

When the heat treatment temperature is higher than 600° C., flocculation of the noble metal is liable to occur so that the mean particle diameter of the noble metal nuclei may become greater than 0.05 $\mu$m. Following the flocculation of the noble metal, the noble metal nuclei may be localized. Accordingly, it is possible that the electrode is liable to peel off from the solid electrolyte.

On the other hand, when the heat treatment temperature is lower than 200° C., it is possible that decomposition of the noble metal compound does not practically occur. Accordingly, deposition of the noble metal nuclei does not advance to disable formation of the nucleus forming portion. Thus, the plating film does not practically adhere to the solid electrolyte so that the solid electrolyte may be partially exposed to the exterior. Further, it is possible that those components, other than the noble metal compound, contained in the solution or carbon produced by those components remain on the surface of the solid electrolyte. In this case, the strong adhesion force between the noble metal nuclei and the solid electrolyte may not be achieved.

In the foregoing first embodiment, the noble metal in the noble metal compound for nucleus formation is platinum. It is preferable that noble metal in a noble metal compound for nucleus formation is at least one selected from the group consisting of Pt, Pd, Au and Rh. These metals have a catalytic function for facilitating plating so that excellent plating is achieved on the solid electrolyte. Further, it is preferable to use an organic noble metal compound as the noble metal compound as in the foregoing first embodiment. The organic noble metal compound makes it easy to adjust viscosity of the solution, thereby making it easy to apply the solution to the electrode forming portion of the solid electrolyte.

In the foregoing first embodiment, the organic platinum compound is contained in the solution at 0.4% by weight. It is preferable that the concentration of the noble metal compound relative to the solution is in the range of 0.05% by weight to 0.4% by weight.

When the concentration is smaller than 0.05% by weight, the amount of the noble metal compound is so small that it may be difficult to form an nucleus forming portion where the noble metal nuclei are uniformly dispersed. In this case, since the strong adhesion force can not be achieved between the plating film and the solid electrolyte, the electrode may be liable to peel off from the solid electrode.

On the other hand, when the concentration exceeds 0.4% by weight, flocculation of the noble metal may be liable to occur to increase the mean particle diameter of the noble metal nuclei to be greater than 0.05 $\mu$m. Following the flocculation of the noble metal, the noble metal nuclei may be localized. Accordingly, it is possible that the electrode is liable to peel off from the solid electrolyte.

Now, the performance evaluation of samples (oxygen sensor elements) produced according to the present invention (hereinafter also referred to as "inventive samples") and comparative samples (oxygen sensor elements) will be described hereinbelow.

Table 1 relates to inventive samples 1–19 while Table 2 relates to comparative samples 20–28. In samples 1–28, organic noble metal compounds were used as noble metal compounds. When noble metal was Pt, dibenzylidene platinum ($C_{16}H_{16}Pt$) was used as an organic noble metal compound and, when noble metal was Pd, balsam palladium ($C_{10}H_{18}SPdCl_x$, where x=1–3) was used as an organic noble metal compound.

The evaluation of samples 1–28 was carried out based on a resistance value test and a peeling test.

A resistance value of each sample was obtained by measuring a dc resistance between the external and internal electrodes at 400° C.

The peeling test was carried out by adhering an adhesive tape to the external electrode and then peeling off the tape. After peeling off the tape, macro-observation and micro-observation of the external electrode were performed. If no peeling of the external electrode was observed both in macro-observation and micro-observation, O was indicated in Table 1 and Table 2.

The macro-observation was performed using a magnifying glass, while the micro-observation was performed using a scanning electron microscope.

Now, the results of the performance evaluation of samples 1–28 will be given hereinbelow.

By comparison between Table 1 and Table 2, it is seen that inventive samples 1–19 all showed low resistance values, meaning that the surface resistances thereof were small. Thus, each inventive ample can ensure an output necessary for detection of the oxygen concentration. As seen from Table 1, the results of the peeling test ere also excellent in all inventive samples 1–19.

On the other hand, comparative samples 20–28 showed large resistance values, and the results of the peeling test were also poor.

Accordingly, it has been confirmed that, in each of the oxygen sensor elements of the inventive samples, the electrode was hard to peel off from the solid electrolyte, the surface resistance at an interface between the electrode and the solid electrolyte was small, and the output necessary for detection of the oxygen concentration was ensured.

As shown in Table 3, an inorganic noble metal compound can also be used as a noble metal compound. In each of inventive samples 29 and 30, the concentration of noble metal in a solution was 0.4% by weight and the heat treatment temperature was 400° C. Like inventive samples 1–19 in Table 1, inventive samples 29 and 30 in Table 3 both showed low resistance values, and the results of the peeling test thereof were also excellent.

TABLE 1

| SAMPLE NO. | NOBLE METAL | NOBLE METAL NUCLEUS MEAN PARTICLE DIAMETER ($\mu$m) | NOBLE METAL CONCENTRATION (% by weight) | HEAT TREATMENT TEMP. (° C.) | RESISTANCE VALUE (k$\Omega$) | PEELING TEST |
|---|---|---|---|---|---|---|
| 1 | Pt | 0.01 | 0.4 | 400 | 9 | O |
| 2 | Pt | 0.007 | 0.1 | 200 | 10 | O |
| 3 | Pt | 0.01 | 0.05 | 600 | 9 | O |
| 4 | Pt | 0.005 | 0.05 | 200 | 10 | O |
| 5 | Pt | 0.04 | 0.4 | 400 | 11 | O |
| 6 | Pt | 0.03 | 0.1 | 600 | 9 | O |
| 7 | Pt | 0.006 | 0.1 | 200 | 11 | O |
| 8 | Pt | 0.008 | 0.05 | 400 | 10 | O |

TABLE 1-continued

| SAMPLE NO. | NOBLE METAL | NOBLE METAL NUCLEUS MEAN PARTICLE DIAMETER (μm) | NOBLE METAL CONCENTRATION (% by weight) | HEAT TREATMENT TEMP. (° C.) | RESISTANCE VALUE (kΩ) | PEELING TEST |
|---|---|---|---|---|---|---|
| 9  | Pt | 0.08  | 0.4  | 600 | 11 | ◯ |
| 10 | Pd | 0.008 | 0.4  | 200 | 11 | ◯ |
| 11 | Pd | 0.01  | 0.1  | 400 | 10 | ◯ |
| 12 | Pd | 0.01  | 0.05 | 600 | 10 | ◯ |
| 13 | Pd | 0.005 | 0.05 | 200 | 9  | ◯ |
| 14 | Pd | 0.03  | 0.4  | 400 | 10 | ◯ |
| 15 | Pd | 0.05  | 0.1  | 600 | 9  | ◯ |
| 16 | Pd | 0.007 | 0.1  | 200 | 10 | ◯ |
| 17 | Pd | 0.01  | 0.06 | 400 | 10 | ◯ |
| 18 | Pd | 0.09  | 0.4  | 600 | 12 | ◯ |
| 19 | Rh | 0.01  | 0.4  | 400 | 10 | ◯ |

TABLE 2

| SAMPLE NO. | NOBLE METAL | NOBLE METAL NUCLEUS MEAN PARTICLE DIAMETER (μm) | NOBLE METAL CONCENTRATION (% by weight) | HEAT TREATMENT TEMP. (° C.) | RESISTANCE VALUE (kΩ) | PEELING TEST |
|---|---|---|---|---|---|---|
| 20 | Pt | *1    | 0.4  | 100 | *2 | X |
| 21 | Pt | 0.11  | 0.4  | 700 | 32 | X |
| 22 | Pd | 0.15  | 0.4  | 900 | *2 | X |
| 23 | Pd | *1    | 0.4  | 100 | *2 | X |
| 24 | Pd | 0.12  | 0.4  | 700 | 96 | X |
| 25 | Pt | 0.18  | 0.4  | 900 | *2 | X |
| 26 | Pt | 0.001 | 0.01 | 600 | *2 | X |
| 27 | Pt | 0.12  | 0.6  | 600 | 30 | X |
| 28 | Rh | 0.15  | 0.4  | 900 | *2 | X |

*1 unmeasurable due to residual binder
*2 resistance value ∞ due to excessive electrode peeling-off

TABLE 3

| SAMPLE NO. | NOBLE METAL COMPOUND | NOBLE METAL NUCLEUS MEAN PARTICLE DIAMETER (μm) | RESISTANCE VALUE (kΩ) | PEELING TEST |
|---|---|---|---|---|
| 29 | $H_2PtCl_6$   | 0.005 | 9  | ◯ |
| 30 | Pt PARTICLES | 0.05  | 12 | ◯ |

Figure 9:
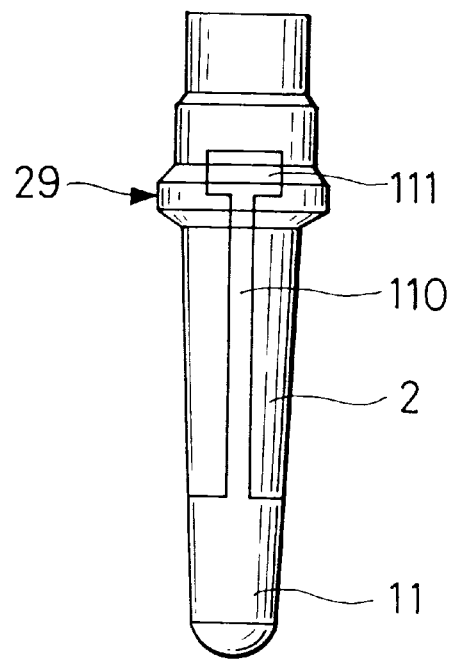
FIG. 9 is a front view showing a modification of the oxygen sensor element according to the first embodiment of the present invention.

In the foregoing first embodiment, the solid electrolyte 2 of the oxygen sensor element 1 is formed with two steps at the upper side of the collar portion 29 as shown in FIGS. 2A and 2B. On the other hand, as shown in FIG. 9, a solid electrolyte 2 having only one step at the upper side of a collar portion 29 may also be used. Further, a solid electrolyte having no step may also be used.

Figure 10A:
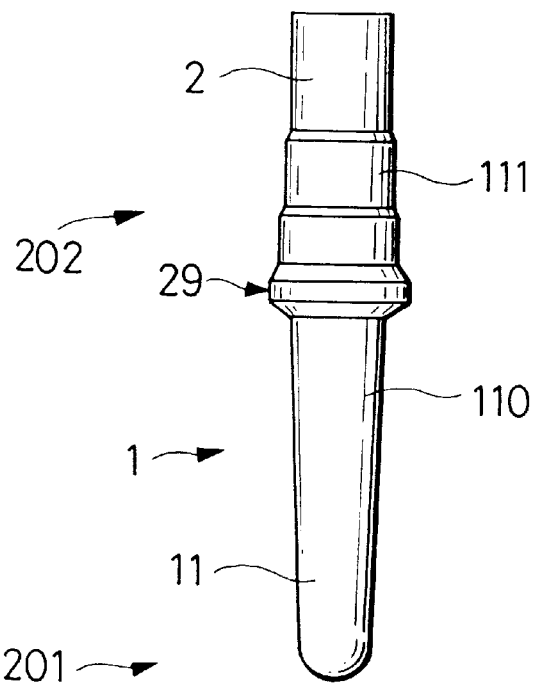
FIG. 10A is a front view showing a modification of the oxygen sensor element according to the first embodiment of the present invention.
Figure 10B:
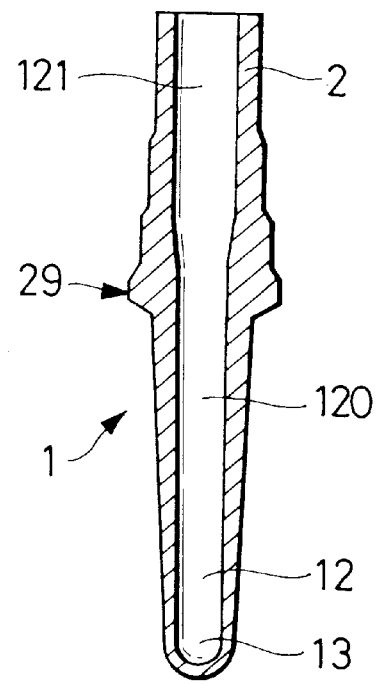
FIG. 10B is a longitudinal-sectional view of the oxygen sensor element shown in FIG. 10A.

FIGS. 10A and 10B show a modification of the oxygen sensor element according to the foregoing first embodiment, wherein a configuration of each of electrode forming portions on a solid electrolyte 2 differs from that of the foregoing first embodiment.

Specifically, as seen from FIG. 10A, a plating film is formed on the outer periphery of the solid electrolyte 2 over a wide range including a tip portion 201 and a trunk portion 202 so as to form a cup-shaped external electrode 11, a cylindrical electrode lead 110 and a cylindrical electrode terminal 111. On the other hand, as seen from FIG. 10B, a plating film is formed all over the inner periphery of the solid electrolyte 2 so as to form a cup-shaped internal electrode 12, a cylindrical electrode lead 120 and a cylindrical electrode terminal 121.

The other structure is the same as the foregoing first embodiment.

Figure 11A:
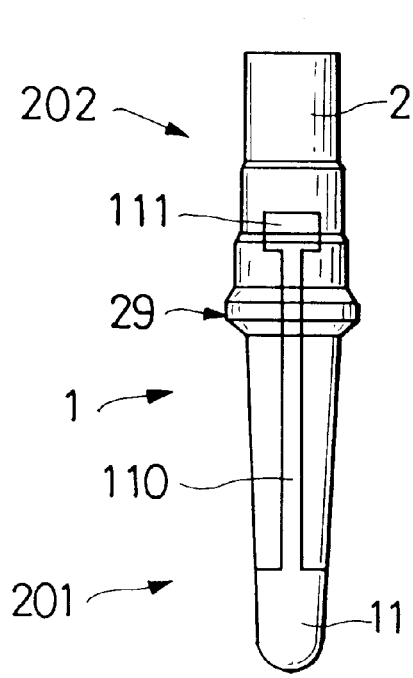
FIG. 11A is a front view showing a modification of the oxygen sensor element according to the first embodiment of the present invention.
Figure 11B:
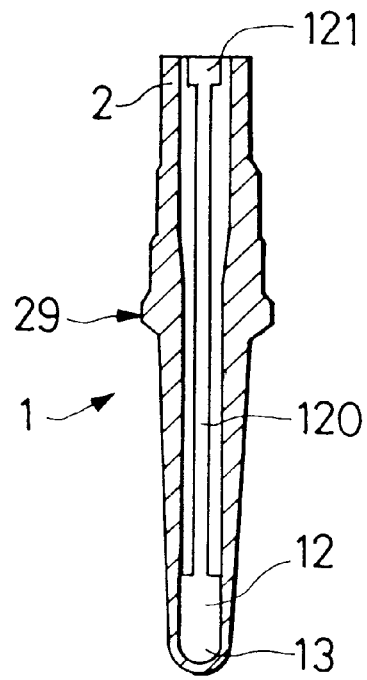
FIG. 11B is a longitudinal-sectional view of the oxygen sensor element shown in FIG. 11A.

FIGS. 11A and 11B show a modification of the oxygen sensor element according to the foregoing first embodiment, wherein a configuration of each of electrode forming portions on a solid electrolyte 2 slightly differs from that of the foregoing first embodiment.

Specifically, as seen from FIG. 11A, an external electrode 11 covers the whole of a tip portion 201 of the solid electrolyte 2 on the outer periphery thereof as opposed to the foregoing first embodiment. Similarly, as seen from FIG. 11B, an internal electrode 12 covers the whole of the tip portion 201 on the inner periphery thereof, and further, electrode terminals 121 are formed on the inner periphery of the solid electrolyte 2.

The other structure is the same as the foregoing first embodiment.

Figure 12A:
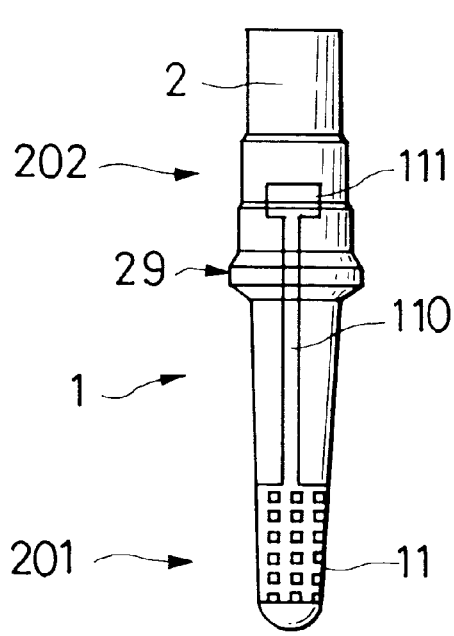
FIG. 12A is a front view showing a modification of the oxygen sensor element according to the first embodiment of the present invention.
Figure 12B:
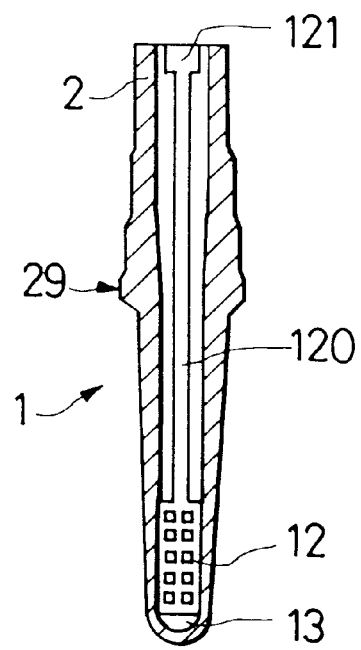
FIG. 12B is a longitudinal-sectional view of the oxygen sensor element shown in FIG. 12A.

FIGS. 12A, 12B and 13 show a modification of the oxygen sensor element according to the foregoing first embodiment, wherein a configuration of each of electrode forming portions on a solid electrolyte 2 slightly differs from that of the foregoing first embodiment.

Specifically, as seen from FIG. 12A, an external electrode 11 is formed into a mesh shape. Similarly, as seen from FIG. 12B, an internal electrode 12 is also formed into a mesh shape, and further, electrode terminals 121 are formed on the inner periphery of the solid electrolyte 2.

The other structure is the same as the foregoing first embodiment.

FIGS. 14A and 14B show a modification of the oxygen sensor element according to the foregoing first embodiment, wherein a configuration of each of electrode forming portions on a solid electrolyte 2 slightly differs from that of the foregoing first embodiment.

Specifically, as seen from FIGS. 14A and 14B, a length of each of an external electrode 11 and an internal electrode 12 is set approximately half the length L1, L2 of the electrode 11, 12 in the foregoing first embodiment, and further, electrode terminals 121 are formed on the inner periphery of the solid electrolyte 2.

The other structure is the same as the foregoing first embodiment.

FIGS. 15A, 15B and 16 show a modification of the oxygen sensor element according to the foregoing first embodiment, wherein a configuration of each of electrode forming portions on a solid electrolyte 2 differs from that of the foregoing first embodiment.

Specifically, in this modification, the number of electrode leads 110 extending from an external electrode 11 is four, and similarly, the number of electrode leads 120 extending from an internal electrode 12 is also four, and further, electrode terminals 121 are formed on the inner periphery of the solid electrolyte 2.

The other structure is the same as the foregoing first embodiment.

In the modification shown in FIGS. 10A and 10B, since the shapes of the electrode forming portions are simple, formation of nucleus forming portions can be easily achieved to facilitate production of the oxygen sensor element.

In the modification shown in FIGS. 11A and 11B, since the electrode forming portions cover the whole of the tip portion 201 on the inner and outer peripheries, the masking operation can be partly omitted upon formation of the nucleus forming portions so that production of the oxygen sensor element can be facilitated.

In the modification shown in FIGS. 12A, 12B and 13, since the external electrode 11 and the internal electrode 12 are formed into the mesh shape, diffusion of oxygen to the solid electrolyte 2 is improved. Thus, the oxygen sensor element 1 is excellent in response characteristic.

The improvement in oxygen diffusion can be achieved when only one of the external electrode 11 and the internal electrode 12 is formed into the mesh shape.

In the modification shown in FIGS. 14A and 14B, the amount of the noble metal to be used can be reduced.

In the modification shown in FIGS. 15A, 15B and 16, even if deterioration occurs to one pair of the electrode leads 110 or 120, the required sensor output can be achieved.

Second Embodiment

Now, the second embodiment of the present invention will be described hereinbelow with reference to FIG. 17.

Figure 17:
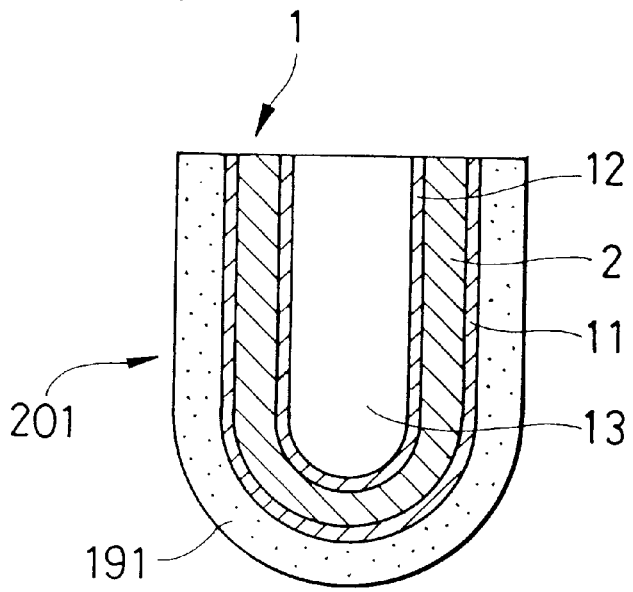
FIG. 17 is a longitudinal-sectional view of an oxygen sensor element at its tip portion according to a second embodiment of the present invention.

As shown in FIG. 17, an oxygen sensor element 1 includes an external electrode 11 and an internal electrode 12 similar to those in the modification shown in FIGS. 11A and 11B. Further, a first protective layer 191 is formed on the external electrode 11 so as to cover the whole of the external electrode 11.

The first protective layer 191 also has a function of a diffusion resistance layer. The first protective layer 191 has a thickness of 100 $\mu$m and a porosity of 20% and is formed of $MgAl_2O_4$ spinel through plasma spraying.

The other structure is the same as the foregoing first embodiment.

In the second embodiment, since the first protective layer 191 is provided on the surface of the external electrode 11, the oxygen sensor element 1 is excellent in durability of the external electrode 11.

Figure 18:
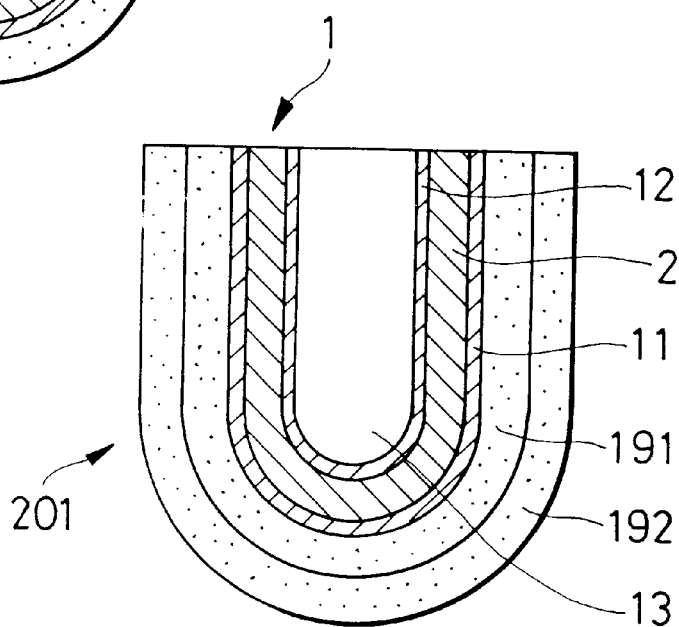
FIG. 18 is a longitudinal-sectional view showing a modification of the oxygen sensor element according to the second embodiment of the present invention.

FIG. 18 shows a modification of the oxygen sensor element according to the foregoing second embodiment. In the modification shown in FIG. 18, the oxygen sensor element 1 further includes a second protective layer 192 formed on the first protective layer 191. The second protective layer 192 has a thickness of 120 $\mu$m and a porosity of 20% to 50% and is made of $Al_2O_3$.

Specifically, the second protective layer 192 can be formed by slurrying $Al_2O_3$, coating the surface of the first protective layer 191 with slurried $Al_2O_3$ using the dip method, and then applying heat treatment thereto.

The other structure is the same as the foregoing second embodiment.

In the modification shown in FIG. 18, in addition to the foregoing effect of the second embodiment, a trap effect is achieved owing to the second protective layer 192. Thus, the oxygen sensor element 1 is further excellent in durability of the external electrode 11.

Figure 19:
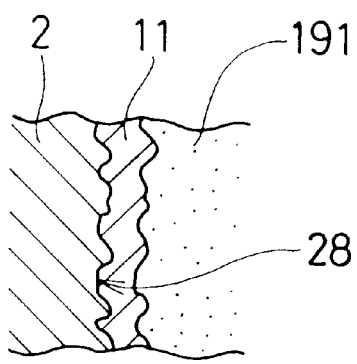
FIG. 19 is a sectional view showing interfaces between a solid electrolyte and an electrode and between the electrode and a protective layer according to a modification of the second embodiment of the present invention.

As shown in FIG. 19, it is preferable that a concavo-convex treatment is applied to the surface of the solid electrolyte 2 for promoting irregularities to be formed thereon. Since the irregularities are promoted on the surface of the solid electrolyte 2 through the concavo-convex treatment, contact areas between the solid electrolyte 2 and the plating film can be Increased, more noble metal nuclei can be in abutment with the plating film, and the plating film can deeply engage with the irregularities on the surface of the solid electrolyte 2. Thus, a strong adhesion force can be exerted between the solid electrolyte 2 and the plating film and thus the electrode. As seen from FIG. 19, the irregularities on the surface of the solid electrolyte 2 can increase not only an adhesive force between the solid electrolyte 2 and the external electrode 11, but also an adhesive force between the external electrode 11 and the first protective layer 191. Thus, the oxygen sensor element 1 having excellent durability can be achieved. The foregoing concavo-convex treatment can be performed by etching, powder application, thermal spraying or the like.

Third Embodiment

Now, the third embodiment of the present invention will be described hereinbelow with reference to FIGS. 20 and 21.

Figure 20:
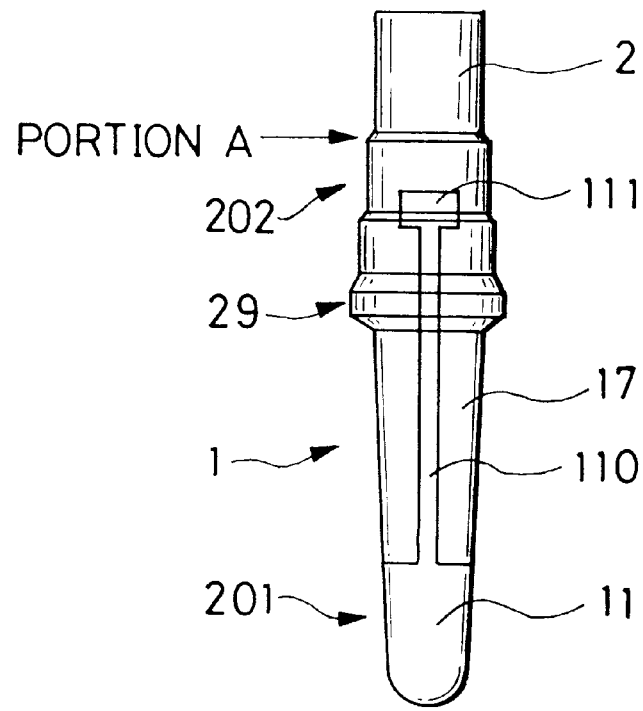
FIG. 20 is a front view of an oxygen sensor element according to a third embodiment of the present invention.
Figure 21:
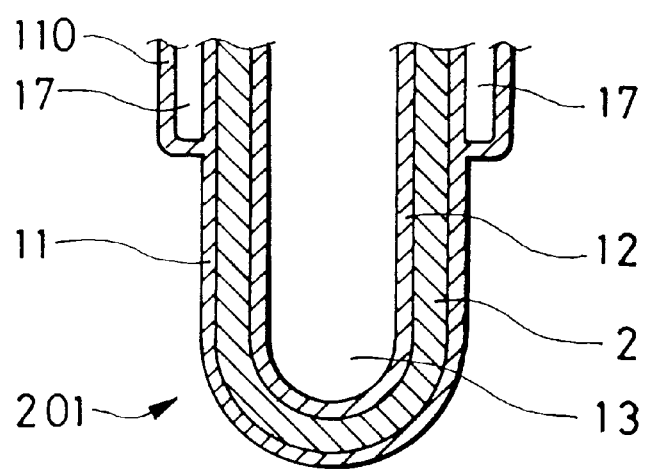
FIG. 21 is a longitudinal-sectional view of the oxygen sensor element at its tip portion shown in FIG. 20.

As shown in FIGS. 20 and 21, an oxygen sensor element 1 includes an insulating layer 17. For producing the oxygen sensor element 1 having the insulating layer 17, a nucleus forming portion is formed on the outer periphery of a solid electrolyte 2 in a range up to a portion A at a trunk portion 202 from the tip of a tip portion 201, and then a plating film is formed on the nucleus forming portion.

Thereafter, as shown in FIG. 20, the insulating layer 17 made of $MgAl_2O_4$ spinel or $Al_2O_3$ is formed on the plating film at portions other than the tip portion 201 working as the external electrode 11.

Then, electrode leads 110 and electrode terminals 111 are formed on the insulating layer 17 so as to be electrically connected to the plating film at the tip portion 201 (see FIG. 21).

Thereafter, by burning the solid electrolyte 2, the oxygen sensor element 1 is obtained.

The other structure is the same as the foregoing first embodiment.

In the oxygen sensor element 1 according to the third embodiment, since the portions whose response characteristics are poor are masked by the insulating layer 17, sensor outputs from those portions are not included in the sensor output so that an excellent response characteristic can be achieved on the whole.

Fourth Embodiment

Now, the fourth embodiment of the present invention will be described hereinbelow with reference to FIGS. 22 and 23.

Figure 22:
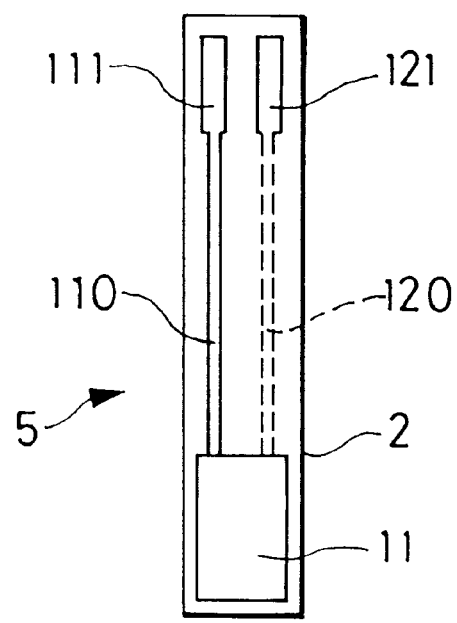
FIG. 22 is a front view of a stacked oxygen sensor element according to a fourth embodiment of the present invention.
Figure 23:
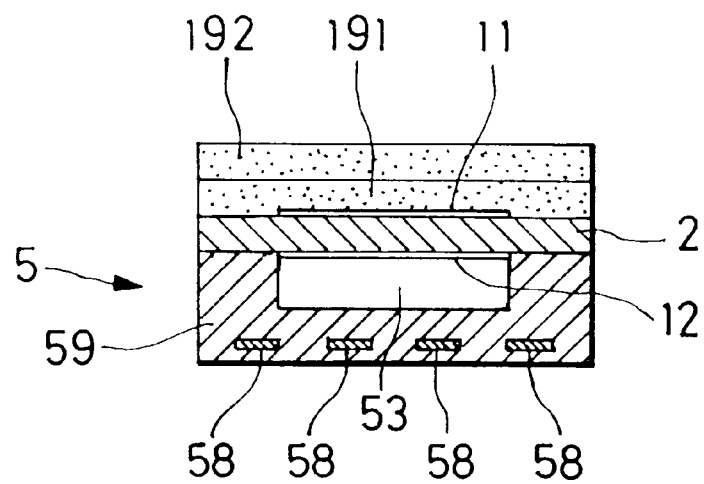
FIG. 23 is a cross-sectional view of the oxygen sensor element shown in FIG. 22.
Figure 24A:
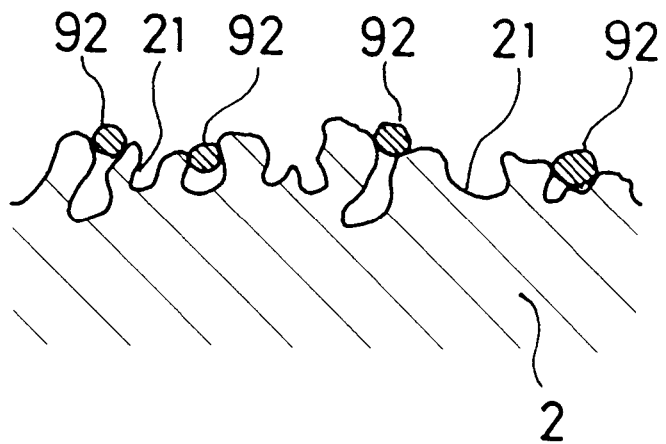
FIG. 24A is an enlarged view of the surface of a solid electrolyte of a conventional oxygen sensor element.
Figure 24B:
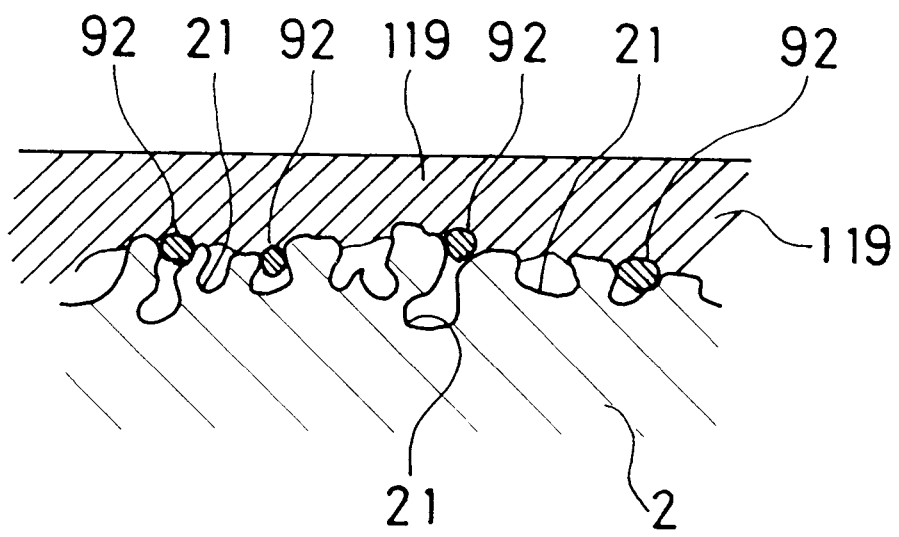
FIG. 24B is an enlarged view of a plating film formed on the surface of the solid electrolyte shown in FIG. 24A.

As shown In FIGS. 22 and 23, the fourth embodiment relates to a stacked oxygen sensor element 5. The stacked oxygen sensor element 5 includes a plate solid electrolyte 2 provided with an external electrode 11 and an internal electrode 12.

The external electrode 11 and the internal electrode 12 are obtained in the same manner as in the foregoing first embodiment, that is, by forming nucleus forming portions on electrode forming portions of the plate solid electrolyte 2, then forming plating films on the nucleus forming portions and burning the plating films.

On the outer side of the solid electrolyte 2 where the external electrode 11 is formed, first and second protective layers 191 and 192 are formed in the order named.

On the inner side of the solid electrolyte 2 where the internal electrode 12 is formed, a heater board 59 having an atmosphere introducing duct and heaters 58 is arranged.

The heater board 59 is a ceramic sheet of Al2O3 formed by press forming, injection molding, sheet forming, lamination or the like.

The external electrode 11 is electrically connected via an electrode lead 110 to an electrode terminal 111 exposed to the exterior. Similarly, the internal electrode 12 is electrically connected via an electrode lead 120 to an electrode terminal 121 exposed to the exterior. The electrode terminals 111 and 121 are formed on an outer surface of the oxygen sensor element 5.

The other structure is the same as the foregoing first embodiment.

As appreciated, the present invention is also applicable to the stacked oxygen sensor element 5. The stacked oxygen sensor element 5 in this embodiment achieves effects similar to those of the foregoing first embodiment. The present invention is further applicable to, for example, a two-cell type stacked oxygen sensor element where electrodes are provided relative to a plurality of solid electrolytes.

While the present invention has been described in terms of the preferred embodiments, the invention is not to be limited thereto, but can be embodied in various ways without departing from the principle of the invention as defined in the appended claims.

What is claimed is:

1. An oxygen sensor element comprising:

a solid electrolyte having cavities on a surface thereof, each of said cavities having finer cavities therein; and an electrode formed on the surface of said solid electrolyte, said electrode in the form of a plating film produced via noble metal nuclei, said noble metal nuclei having a mean particle diameter of no greater than 0.05 $\mu$m and provided only on the surface of said solid electrolyte so as to be located in said cavities and further in said finer cavities, so that said electrode enters said cavities and further enters said finer cavities for ensuring adhesion of said electrode relative to the surface of said solid electrolyte.

* * * * *